US011980612B2

(12) United States Patent
Richards et al.

(10) Patent No.: US 11,980,612 B2
(45) Date of Patent: *May 14, 2024

(54) SYNERGISTIC ANTI-INFLAMMATORY COMPOSITIONS

(71) Applicant: The Procter & Gamble Company, Cincinnati, OH (US)

(72) Inventors: Jeanette Anthea Richards, Liberty Township, OH (US); James Robert Schwartz, West Chester, OH (US); Leo Timothy Laughlin, II, Mason, OH (US); Geoffrey Marc Wise, Reading, OH (US); Eric Scott Johnson, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/126,380

(22) Filed: Dec. 18, 2020

(65) Prior Publication Data

US 2021/0401818 A1 Dec. 30, 2021

Related U.S. Application Data

(60) Provisional application No. 63/044,807, filed on Jun. 26, 2020.

(51) Int. Cl.
*A61K 31/4412* (2006.01)
*A61K 9/00* (2006.01)
*A61K 31/216* (2006.01)
*A61K 31/505* (2006.01)

(52) U.S. Cl.
CPC ........ *A61K 31/4412* (2013.01); *A61K 9/0014* (2013.01); *A61K 31/216* (2013.01); *A61K 31/505* (2013.01)

(58) Field of Classification Search
CPC ................................................ A61K 31/4412
See application file for complete search history.

(56) References Cited

U.S. PATENT DOCUMENTS

| | | | |
|---|---|---|---|
| 4,796,812 A | 1/1989 | Grollier | |
| 4,885,107 A | 12/1989 | Wetzel | |
| 5,624,666 A | 4/1997 | Coffindaffer et al. | |
| 5,675,013 A | 10/1997 | Hani et al. | |
| 6,060,044 A | 5/2000 | Cretois | |
| 8,360,973 B2 | 1/2013 | Bazin | |
| 9,034,792 B2 | 5/2015 | Stark et al. | |
| 9,126,163 B2 | 9/2015 | Giessler-blank et al. | |
| 9,996,674 B2 | 6/2018 | Segman | |
| 10,227,551 B2 | 3/2019 | Arhancet et al. | |
| 10,543,157 B2 | 1/2020 | Davis | |
| 10,925,823 B2 | 2/2021 | Schwartz | |
| 11,433,015 B2 | 9/2022 | Oh et al. | |
| 11,433,070 B2 * | 9/2022 | Richards | A61K 8/4953 |
| 11,701,316 B2 | 7/2023 | Richards et al. | |
| 2002/0150287 A1 | 10/2002 | Kobayashi | |
| 2002/0183988 A1 | 12/2002 | Skaanning | |
| 2003/0215522 A1 | 11/2003 | Johnson | |
| 2004/0213751 A1 | 10/2004 | Schwartz | |
| 2008/0220103 A1 | 9/2008 | Birnbaum et al. | |
| 2009/0155383 A1 | 6/2009 | Kitko et al. | |
| 2009/0222956 A1 | 9/2009 | Cush et al. | |
| 2009/0274642 A1 | 11/2009 | Dawson, Jr. et al. | |
| 2010/0106679 A1 | 4/2010 | Yamaguchi | |
| 2010/0234366 A1 | 9/2010 | Van Ravenzwaay et al. | |
| 2011/0055978 A1 | 3/2011 | Jamet et al. | |
| 2011/0190129 A1 | 8/2011 | Bell et al. | |
| 2011/0195846 A1 | 8/2011 | Troppmann et al. | |
| 2011/0217340 A1 | 9/2011 | Angus et al. | |
| 2012/0022021 A1 | 1/2012 | Rademacher et al. | |
| 2012/0309733 A1 | 12/2012 | Chang et al. | |
| 2013/0064900 A1 | 3/2013 | Hening | |
| 2013/0196852 A1 | 8/2013 | Rannard et al. | |
| 2013/0197275 A1 | 8/2013 | Spiegler et al. | |
| 2014/0028822 A1 | 1/2014 | Khadavi | |
| 2014/0071456 A1 | 3/2014 | Podoleanu et al. | |
| 2014/0120048 A1 | 5/2014 | Krueger | |
| 2014/0171471 A1 | 6/2014 | Krueger | |
| 2014/0271930 A1 | 9/2014 | Kerr et al. | |
| 2014/0273055 A1 | 9/2014 | Kerr et al. | |
| 2014/0378810 A1 | 12/2014 | Davis | |
| 2015/0010487 A1 | 1/2015 | Snyder et al. | |
| 2015/0217465 A1 | 8/2015 | Krenik | |
| 2015/0272865 A1 | 10/2015 | Mette | |
| 2015/0313819 A1 | 11/2015 | Edelson | |

(Continued)

FOREIGN PATENT DOCUMENTS

CN 102715187 A 10/2012
CN 104000749 B 9/2016

(Continued)

OTHER PUBLICATIONS

Machine translation of CN 110025628A1, Jul. 19, 2019 (Year: 2019).*
Written Opinion of PCT/US2020/065812. (Year: 2020).*
Turner et al. "Stratum Corneum Dysfunction in Dandruff", International Journal of Cosmetic Science, 34, Feb. 24, 2012, pp. 298-306.
PCT Search Report and Written Opinion for PCT/US2020/065812 dated May 4, 2021,14 pages.
All Office Actions; U.S. Appl. No. 16/913,191, filed Jun. 26, 2020.
All Office Actions; U.S. Appl. No. 17/126,387, filed Dec. 18, 2020.
All Office Actions; U.S. Appl. No. 17/126,393, filed Dec. 18, 2020.
All Office Actions; U.S. Appl. No. 17/126,932, filed Dec. 18, 2020.
All Office Actions; U.S. Appl. No. 17/126,958, filed Dec. 18, 2020.
All Office Actions; U.S. Appl. No. 16/913,183, filed Jun. 26, 2020.
All Office Actions; U.S. Appl. No. 17/126,975, filed Dec. 18, 2020.

(Continued)

*Primary Examiner* — John S Kenyon
*Assistant Examiner* — Gillian A Hutter
(74) *Attorney, Agent, or Firm* — Linda M. Sivik

(57) ABSTRACT

The present invention is directed to a personal composition comprising a) a strobilurin; b) a 2-pyridinol-N-oxide material wherein the ratio of a:b is from about 10:1 to about 1:20; wherein there is a synergistic anti-inflammatory/cellular stress activity.

11 Claims, No Drawings

(56) References Cited

U.S. PATENT DOCUMENTS

| | | | |
|---|---|---|---|
| 2016/0038397 | A1 | 2/2016 | Markland |
| 2016/0310393 | A1 | 10/2016 | Chang |
| 2016/0346184 | A1 | 12/2016 | Schwartz et al. |
| 2017/0135932 | A1 | 5/2017 | Schwartz et al. |
| 2017/0225006 | A1 | 8/2017 | Anderson |
| 2017/0270593 | A1 | 9/2017 | Sherman |
| 2017/0304172 | A1 | 10/2017 | Chang et al. |
| 2017/0367963 | A1 | 12/2017 | Kadir |
| 2018/0040052 | A1 | 2/2018 | Robinson |
| 2018/0225673 | A1 | 8/2018 | Dubey |
| 2018/0311135 | A1 | 11/2018 | Chang et al. |
| 2018/0311136 | A1 | 11/2018 | Chang et al. |
| 2018/0325791 | A1 | 11/2018 | Lane et al. |
| 2019/0035149 | A1 | 1/2019 | Chen |
| 2019/0105243 | A1 | 4/2019 | Song et al. |
| 2019/0105244 | A1 | 4/2019 | Song et al. |
| 2019/0105245 | A1 | 4/2019 | Song et al. |
| 2019/0117543 | A1 | 4/2019 | Zhao et al. |
| 2019/0313637 | A1 | 10/2019 | Seelmann-eggebert et al. |
| 2019/0350514 | A1 | 11/2019 | Purwar |
| 2019/0350819 | A1 | 11/2019 | Hamersky |
| 2019/0355115 | A1 | 11/2019 | Niebauer |
| 2019/0381055 | A1 | 12/2019 | Cong |
| 2020/0000690 | A1 | 1/2020 | Renock et al. |
| 2020/0061018 | A1 | 2/2020 | Lawyer et al. |
| 2020/0163334 | A1 | 5/2020 | Albright et al. |
| 2020/0163905 | A1 | 5/2020 | Mendrok-edinger et al. |
| 2020/0214953 | A1 | 7/2020 | Lane |
| 2021/0069091 | A1 | 3/2021 | Oh et al. |
| 2021/0283131 | A1* | 9/2021 | Richards ............... A61P 17/10 |
| 2021/0401707 | A1 | 12/2021 | Johnson et al. |
| 2021/0401710 | A1 | 12/2021 | Johnson et al. |
| 2022/0202677 | A1* | 6/2022 | Stephens ............... B26B 21/22 |

FOREIGN PATENT DOCUMENTS

| | | | | |
|---|---|---|---|---|
| CN | 109620896 | A | | 4/2019 |
| CN | 109700877 | A | | 5/2019 |
| CN | 109757493 | A | | 5/2019 |
| CN | 105434465 | B | | 7/2019 |
| CN | 110025658 | A | | 7/2019 |
| CN | 110025658 | A | * | 7/2019 ............ A61K 36/14 |
| CN | 110420131 | A | | 11/2019 |
| DE | 102012203240 | A1 | | 3/2013 |
| KR | 1020120018739 | A | | 3/2012 |
| WO | 9939683 | A1 | | 8/1999 |
| WO | 0069410 | A1 | | 11/2000 |
| WO | 0200027 | A1 | | 1/2002 |
| WO | 2012040804 | A2 | | 4/2012 |
| WO | 2012058557 | A2 | | 5/2012 |
| WO | 2014073456 | A1 | | 5/2014 |
| WO | WO-2014165253 | A1 | * | 10/2014 ............ A01N 25/02 |
| WO | 2014208162 | A1 | | 12/2014 |
| WO | 2017009206 | A1 | | 1/2017 |
| WO | 2019166521 | A1 | | 9/2019 |
| WO | 2020264577 | A1 | | 12/2020 |
| WO | WO-2020264577 | A1 | * | 12/2020 ......... A61K 31/4412 |

OTHER PUBLICATIONS

Andrew J. Wiemer et al., "A live imaging cell motility screen identifies prostaglandin E 2 as a T cell stop signal antagonist", The Journal of Immunology, vol. 187, No. 7, Oct. 1, 2011, 9 pgs.

Anonymous: "Mixtures of fungicides and insecticides", Research disclosure, Kenneth Mason Publications, Hampshire UK, GB, vol. 338, No. 93, Jun. 1, 1992, 9 pgs.

Hyun Seung Wi et al., "The anti-fungal effect of light emitting diode on yeasts", Journal of Dermatological Science, vol. 67, No. 1, Apr. 4, 2012, pp. 3-8.

Pierard-Franchimont C et al: "Effect of residence time on the efficacy of antidandruff shampoos", International Journal of Cosmetic Science, Jun. 30, 2003 (Jun. 30, 2003), XP055794760,DOI: 10.IIII/j.1467-2494.2003.00195.x Retrieved from the Internet:URL:https://doi.org/10.IIII/j.1467-2494.2003.00195.x[retrieved on Apr. 13, 2021] "Introduction" 6 pgs.

Pierard-Franchimont C., et al., "Revisiting dandruff", International Journal of Cosmetic Science, Kluwer Academic Publishers, Dordrecht, NL, vol. 28, No. 5, Oct. 1, 2006, pp. 311-318.

Unpublished U.S. Appl. No. 17/126,932, filed Dec. 18, 2020, to Jeanette Anthea Richards et. al.

Unpublished U.S. Appl. No. 17/126,958, filed Dec. 18, 2020, to Jeanette Anthea Richards et. al.

Unpublished U.S. Appl. No. 17/126,975, filed Dec. 18, 2020, to Jeanette Anthea Richards et. al.

C.C. Zouboulis et al. "Acne is an inflammatory disease and alterations of sebum composition initiate acne lesions", J Eur Acad Dermatol Venereol, 2014, vol. 28, Issue 5, pp. 527-532.

K.J. Mills et al. "Dandruff/seborrhoeic dermatitis is characterized by an inflammatory genomic signature and possible immune dysfunction: transcriptional analysis of the condition and treatment effects of zinc pyrithione", British Journal of Dermatology, 2012 vol. 166, pp. 33-40.

P. Mondon et al. "Reinforcement of barrier function and scalp homeostasis by Senkyunolide A to fight against dandruff", International Journal of Cosmetic Science, 2017, vol. 39, pp. 617-621.

Paterson "Salicylic acid: a link between aspirin, diet and the prevention of colorectal cancer", QJM, Aug. 2001, vol. 94(8); pp. 2.

Advanced Fungal Chemistry/Liu Jikai, editor. Beijing: China Science and Technology Press, Jun. 2004; ISBN 7-5046-3819-6, Year 2004, pp. 14.

Research and Introduction of Biopesticides / Authors: Yang Ye, Harbin: Heilongjiang Science and Technology Press, Publication Date: Dec. 2008; ISBN: 978-7-5388-5888-4, 07 Pages.

Safety and Technical Standards for Cosmetics, Year 2015, pp. 02.

"Anti-Dandruff Treatment Hair Cream", Mintel, Sep. 3, 2018, 3 pgs.

"Balancing and Anti-Dandruff Shampoo", Mintel, Jan. 6, 2014, 3 pgs.

"Double Care Anti-Dandruff Treatment Hair Cream", Mintel, Oct. 16, 2012, 2 pgs.

"Hair Lotion", Mintel, Oct. 7, 2019, 3 pgs.

"Moist-Up Eye Cream", Mintel, Nov. 11, 2009, 5 Pgs.

"Moisturizing Anti-Dandruff Shampoo", Mintel, Mar. 17, 2016, 2 pgs.

Anwar et al. "Size and shape dependent clinical and mycological efficacy of silver nanoparticles on dandruff", International Journal of Nanomedicine, 2016, pp. 147-161.

Schwartz et al., "The role of oxidative damage in poor scalp health: ramifications to causality and associated hair growth", International Journal of Cosmetic Science, vol. 37, No. Suppl. 2, 2015, pp. 9-15.

* cited by examiner

SYNERGISTIC ANTI-INFLAMMATORY COMPOSITIONS

FIELD OF THE INVENTION

The present invention relates to personal care compositions comprising a 2-pyridinol-N-oxide material and a strobilurin demonstrating synergistic anti-inflammatory activity.

BACKGROUND OF THE INVENTION

Optimal health of the hair, scalp and skin is dependent on control of cellular stress and the ability to counteract or remove insults by appropriate protective mechanisms. Cellular stress may be triggered by reactive oxygen species, pollution, toxins, microorganisms, mechanical or chemical insults and several other extrinsic or intrinsic factors. Prolonged, unresolved or high levels of cellular stress is manifested in the decline of hair, scalp or skin health with visible signs of damage (e.g. hair loss, loss of hair or skin pigmentation, scalp or skin dryness, flaking, itching) and both accelerated and chronological aging. Cellular responses to pathological stress converge on inflammation as a major, common mechanism and excessive inflammation contributes to reduced health and several stress-related conditions. Chronic inflammatory disorders of the skin such as dandruff and acne have widespread prevalence, and both involve microorganisms on the skin that produce substances which trigger and exacerbate inflammation.

There is a need for improved products that address and resolve inflammation and cellular stress in chronic disorders of the skin, scalp and hair. Personal care products are also desired that reduce cellular stress and provide consumers with healthier, hair, scalp and skin and enhanced anti-aging benefits.

SUMMARY OF THE INVENTION

The present invention is directed to a personal composition comprising a) a strobilurin; b) a 2-pyridinol-N-oxide material wherein the ratio of a:b is from about 10:1 to about 1:20; wherein there is a synergistic anti-inflammatory/cellular stress activity.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Where amount ranges are given, these are to be understood as being the total amount of said ingredient in the composition, or where more than one species fall within the scope of the ingredient definition, the total amount of all ingredients fitting that definition, in the composition.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Strobilurins

Strobilurins are a general class of compounds used as agricultural fungicides that are inspired from natural fungal metabolites. Strobilurins are either biosynthesized as a natural product by various Basidiomycete fungi such as *Strobilurus tenacellus* and *Oudemansiella mucida* or modeled after natural strobilurins and synthesized with retention of the key β-methoxyacrylate toxophore. Some synthesized strobilurins have a modified toxophore e.g. methyl methoxyiminoacetate or methyl-N-methoxycarbamate. Some synthetic strobilurins are azoxystrobin (CAS number: 131860-33-8), coumoxystrobin (CAS number 850881-70-8), dimoxystrobin (CAS number 149961-52-4), enoxastrobin (CAS number 238410-11-2), fluoxastrobin (CAS number 193740-76-0), kresoxim methyl (CAS number 143390-89-0), mandestrobin (CAS number 173662-97-0), metominostrobin (CAS number 133408-50-1), orysastrobin (CAS number 248593-16-0), picoxystrobin (CAS number 117428-22-5), pyraclostrobin (CAS number 175013-18-0), pyraoxystrobin (CAS number 862588-11-2), and trifloxystrobin (CAS number 141517-21-7).

Strobilurins control a broad spectrum of plant fungal diseases and are used heavily in crop protection worldwide. They work to inhibit fungal growth by inhibition of mitochondrial respiration. The specific mode of action of strobilurins is by binding the ubiquinol oxidizing site ($Q_0$ site) in the cytochrome b complex III of the electron transport chain and blocking electron transfer between cytochrome b and cytochrome $c_1$. Other compounds with this specific mode of action include synthetic and naturally occurring derivatives of the key β-methoxyacrylate toxophore known as oudemansins also first isolated from *Oudemansiella mucida*, synthetic and naturally occurring myxothiazols from myxobacteria such as *Myxococcus flavus*, stigmatellins from myxobacteria such as *Stigmatella aurantica* and the synthetic agricultural chemicals famoxadone and fenamidone.

Azoxystrobin, is an example of an agricultural fungicide belonging to the class of strobilurins. Azoxystrobin as an agricultural fungicide has protectant, curative, eradicant, translaminar and systemic properties and inhibits spore germination and mycelial growth, and also shows antisporulant activity. At labelled application rates, azoxystrobin controls the numerous plant pathogens including *Erysiphe graminis*, *Puccinia* spp., *Lepiosphaeria nodorum*, *Septoria tritici* and *Pyrenophora teres* on temperate cereals; *Pyricularia oryzae* and *Rhizoctonia solani* on rice; *Plasmopara viticola* and *Uncinula necator* on vines; Sphaerotheca *fuliginea* and *Pseudoperonospora cubensis* on cucurbitaceae; *Phytophthora infestans* and *Alternaria solani* on potato and tomato; *Mycosphaerella arachidis*, *Rhizoctonia solani* and *Sclerotium rolfsii* on peanut; *Monilinia* spp. and *Cladosporium carpophilum* on peach; *Pythium* spp. and *Rhizoctonia solani* on turf; *Mycosphaerella* spp. on banana; *Cladosporium caryigenum* on pecan; *Elsinoe fawcetii*, *Colletotrichum* spp. and *Guignardia citricarpa* on citrus; *Colletotrichum* spp. and *Hemileia vastatrix* on coffee. Azoxystrobin is a solid material having low solubility in water.

Some tradenames for azoxystrobin include ABOUND FLOWABLE FUNGICIDE, Aframe, Azoxystar, Azoxyzone, AZteroid 1.65 SC Fungicide, AZURE AGRICULTURAL FUNGICIDE, Endow, QUADRIS FLOWABLE FUNGICIDE, Satori Fungicide, Strobe 2L, and Willowood Azoxy 2SC. Azoxystrobin is commercially available from for example Sigma-Aldrich (St. Louis, MO) and Ak Scientific, Inc (Union City, CA).

In the present invention, the personal care composition may contain from about 0.02% to about 10% of azoxystrobin; from about 0.05% to about 2% of azoxystrobin; from about 0.1% to about 1% of azoxystrobin.

In the present invention, the personal care composition may contain from about 0.02% to about 10% of a strobilurin; from about 0.05% to about 2% of a strobilurin; from about 0.1% to about 1% of a strobilurin.

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

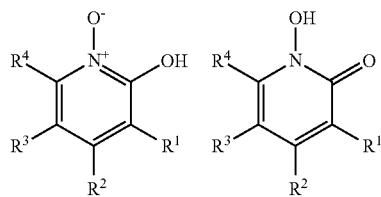

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $^+N(R^7R^8R^9R^{10})$, and 1/q $M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $½Mg^{2+}$, or $½Ca^{2+}$, substituted ammonium, such as $C_1$-$C_6$ alkanolammnonium, mono-ethanolamine (MEA), triethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, MO) and/or Aces Pharma (Branford, CT).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, MO), Princeton Building Blocks (Monmouth Junction, NJ), 3B Scientific Corporation (Libertyville, IL), SynFine Research (Richmond Hill, ON), Ryan Scientific, Inc. (Mt. Pleasant, SC), and/or Aces Pharma (Branford, CT).

In certain aspects, the 2-pyridinol-N-oxide material is a 2-pyridinol-N-oxide material or tautomer thereof according to the formula(s) below:

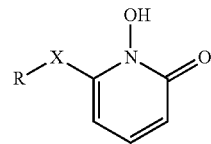

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

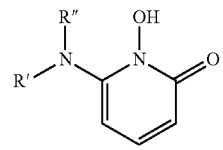

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

In the present invention, the personal care composition may contain from about 0.1% to about 10% of a substituted or unsubstituted 2-pyridinol N-oxide material. Alternatively, the hair care composition may contain from about 0.3% to about 3% of a substituted or unsubstituted 2-pyridinol N-oxide material. Alternatively, the hair care composition may contain from about 0.5% to about 2% of a substituted or unsubstituted 2-pyridinol N-oxide material.

Other Anti-Microbial Actives

The present invention may comprise scalp health agents selected from polyvalent metal salts of pyrithione, and may further comprise one or more anti-fungal or anti-microbial actives. Suitable anti-microbial actives include coal tar, sulfur, whitfield's ointment, castellani's paint, aluminum chloride, gentian violet, ciclopirox olamine, undecylenic acid and its metal salts, potassium permanganate, selenium sulfide, sodium thiosulfate, propylene glycol, oil of bitter orange, urea preparations, griseofulvin, 8-Hydroxyquinoline, clioquinol, thiobendazole, thiocarbamates, haloprogin, polyenes, hydroxypyridone, morpholine, benzylamine, allylamines (such as terbinafine), tea tree oil, neem, clove leaf oil, coriander, palmarosa, berberine, thyme red, cinnamon oil, cinnamic aldehyde, citronellic acid, hinokitiol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. In the present invention, anti-microbials may include itraconazole, ketoconazole, selenium sulfide and coal tar.

b. Selenium Sulfide

Selenium sulfide is a particulate scalp health agent suitable for use in the anti-microbial compositions of the present invention. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), and in the present invention, may be less than 10 μm. Selenium sulfide compounds are described, for example, in U.S. Pat. Nos. 2,694,668; 3,152,046; 4,089,945; and 4,885,107.

c. Sulfur

Sulfur may also be used as a particulate anti-microbial/scalp health agent in the anti-microbial compositions of the present invention.

d. Keratolytic Agents

The present invention may further comprise one or more keratolytic agents such as Salicylic Acid.

The present invention may also comprise a combination of surfactant soluble anti-scalp health agents and particulate scalp health agents. In the present invention, the combination of anti-microbial active may be selected from the group of combinations consisting of: piroctone olamine and zinc pyrithione, pine tar and sulfur, salicylic acid and zinc pyrithione, salicylic acid and elubiol, zinc pyrithione and elubiol, zinc pyrithione and climbazole, piroctone olamine and climbazole, salicylic acid and piroctone olamine, and mixtures thereof.

e. Additional Anti-Microbial Actives

Additional anti-microbial actives of the present invention may include extracts of *melaleuca* (tea tree) and charcoal. The present invention may also comprise combinations of anti-microbial actives. Such combinations may include piroctone olamine and zinc pyrithione combinations, pine tar and sulfur combinations, salicylic acid and zinc pyrithione combinations, piroctone olamine and climbazole combinations, and salicylic acid and piroctone olamine combinations, zinc pyrithione and climbazole and mixtures thereof.

In the present invention, the scalp health agent may be present in an amount from about 0.01% to 10%, may be from about 0.1% to 9%, may be from about 0.25% to 8%, may be from about 0.5% to 6%.

In the present invention, the composition may comprise an effective amount of a zinc-containing layered material. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In the present invention, the ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In the present invention, the ZLM may be a layered double hydroxide conforming to the formula $[M^{2+}_{1-x}M^{3+}_x(OH)_2]^{x+}A^{n-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In the present invention, the ZLM may be a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+}2x\ A^- \cdot nH_2O$. This latter formula represents (where x=0.4) materials such as zinc hydroxychloride and zinc hydroxynitrate. In the present invention, the ZLM may be zinc hydroxychloride and/or zinc hydroxynitrate. These are related to hydrozincite as well wherein a divalent anion replace the monovalent anion. These materials can also be formed in situ in a composition or in or during a production process.

In the present invention, the composition may comprise basic zinc carbonate. Commercially available sources of basic zinc carbonate include Zinc Carbonate Basic (Cater Chemicals: Bensenville, IL, USA), Zinc Carbonate (Shepherd Chemicals: Norwood, OH, USA), Zinc Carbonate (CPS Union Corp.: New York, NY, USA), Zinc Carbonate (Elementis Pigments: Durham, UK), and Zinc Carbonate AC (Bruggemann Chemical: Newtown Square, PA, USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In an the present invention, the composition may comprise an effective amount of a zinc-containing layered material. In the present invention, the composition may comprise from about 0.001% to about 10%, or from about 0.01% to about 7%, or from about 0.1% to about 5% of a zinc-containing layered material, by total weight of the composition.

The present invention may have a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

PGE-2 Assay

Inhibiting the Cell's Inflammation Response to a Stressor-Prostaglandin E2 ("PGE2") Assay.

This example demonstrates the ability of azoxystrobin and piroctone olamine (PO) combinations to inhibit PGE2 activation in a synergistic manner at some specific ratios. PGE2 is a hormone-like substance that is known to participate in modulation of inflammation. Cellular inflammation is associated with a variety of hair, skin and scalp conditions, and thus inhibiting PGE2 activation vis-à-vis cellular inflammation may help treat these types of hair, skin and scalp conditions.

Method

TERT keratinocytes ("tKC" are human keratinocytes which have been transfected with the human telomerase reverse transcriptase gene to immortalize the cells) were obtained from Jerry Shay, University of Texas, Southwestern and plated at 40,000 cells/well into 24-well plates in 1 ml/well volume. EpiLife Medium (Life Technologies cat #MEPICFPRF500) supplemented with keratinocyte growth supplement (Life technologies cat #S-001-5) was used as the assay media. The cells were grown to confluence/near confluence, (typically 24 hours after plating 40,000 cells/well in 24 well plate) and then subjected to 15 mJ/cm$^2$ UVB-stress (typically 14-16 exposure time in BioSun). The test compositions (strobilurins, piroctone olamine, strobilurins+piroctone olamine, and positive control 10 uM idebenone) were added to replace the medium (EpiLife Medium with 0.1% final concentration of DMSO—briefly, 1000× stocks of actives and combinations made in 100% DMSO and diluted into Epilife media 1 to 1000), and the plates were incubated for 18-24 hours.

The supernatant is removed from each well, and the cells are rinsed with 2 ml/well medium (without supplements). A Cell Titer-Glo assay (Promega cat #G7571; Madison WI) is used to measure ATP activity, is conducted on the cells for normalization. The supernatant is tested in a PGE2 assay (Prostaglandin E2 Assay kit from Cisbio Bioassays cat #62P2APEB) according to the manufacturer's instructions. The PGE2 results are normalized to ATP activity. The PGE2 quantitation (pg/mL) from the supernatant is divided by the normalization factor (treatment ATP/control ATP).

Example Calculation to Compute PGE2 Inhibition by Strobilurin:

Luminescence of vehicle control in ATP assay=704567
Luminescence of strobilurin treatment in ATP assay=678903
Normalization factor for strobilurin treatment=1.038
PGE2 quantitation for vehicle control=2458 pg/mL PGE2
PGE2 quantitation for strobilurin treatment=2347 pg/mL PGE2
Normalized PGE2 values
control=2458/1=2458
strobilurin=2347/1.038=2261
% inhibition for strobilurin=[100×(2458−2347)/2458]=8%

Student's T-Test (equal variance, 2 sided) are used to calculate p-values between observed combinations and expected combinations with p-value<0.05 considered statistically significant. Expected combination values are calculated by adding the PGE2 inhibition values of strobilurins alone and piroctone olamine alone. Synergy factor is simply the ratio of observed combination/expected combination. Synergy factors greater than 1.0 with a p-value<0.05 are deemed synergistic.

The conclusion of the PGE2 experiments is that even though strobilurins and piroctone olamine are relatively weak materials individually in inhibiting PGE2 release from keratinocytes, combinations of strobilurin and piroctone olamine do in fact surprisingly suppress PGE2 release. Other strobilurins also synergistically inhibit PGE2 release as well. Multiple ratios of azoxystrobin to piroctone olamine have been tested to define the ratios at which the synergistic inhibition of PGE2 release occurs and at Azoxystrobin: piroctone olamine ratio of 1:1 and 1:10 there is statistically significant synergy. At Azoxystrobin: piroctone olamine ratio of 4:1 and 1:50, there is not statistically significant synergy, but the combination does in fact show additivity in reducing PGE2 release at these ratios.

In the present invention, another strobilurin and piroctone olamine may demonstrate combinations of a strobilurin and piroctone olamine (PO) that do in fact also surprisingly suppress PGE2 release and synergistic inhibition of PGE2 release may occur at a strobilurin:PO ratio of 1:1 and 1:10.

| | strobilurin w/v % | | | |
| --- | --- | --- | --- | --- |
| | $4 \times 10^{-7}$ | $1 \times 10^{-7}$ | $1 \times 10^{-8}$ | $1 \times 10^{-9}$ |
| | PO w/v % | | | |
| | $1 \times 10^{-7}$ | $1 \times 10^{-7}$ | $1 \times 10^{-7}$ | $1 \times 10^{-7}$ |
| | strobilurin:PO ratio | | | |
| | 4:1 | 1:1 | 1:10 | 1:50 |
| Treatment | % PGE$_2$ Inhibition | | | |
| azoxystrobin | 13 | 8 | 1 | 1 |
| PO | 2.8 | 3.2 | 2.6 | 2.4 |
| azoxystrobin + PO (observed) | 20.1 | 32.1* | 22.6* | 5 |
| azoxystrobin + PO (expected) | 15.8 | 11.2 | 3.6 | 3.4 |
| synergy factor | 1.27 | 2.87 | 6.28 | 1.47 |
| p-value observed vs expected | 0.34 | 0.007* | 0.013* | 0.78 |
| trifloxystrobin | 8.3 | 3.2 | 0.5 | 0.7 |
| PO | 2.8 | 3.2 | 2.6 | 2.4 |
| trifloxystrobin + PO (observed) | 14.1 | 46.7* | 1.7 | 2.1 |
| trifloxystrobin + PO (expected) | 11.1 | 6.4 | 3.1 | 3.1 |
| synergy factor | 1.27 | 7.29 | 0.54 | 0.69 |
| p-value observed vs expected | 0.67 | 0.002* | 0.45 | 0.69 |
| orysastrobin | 4.7 | 8.2 | 15.6 | 1.1 |
| PO | 2.8 | 3.2 | 2.6 | 2.4 |
| orysastrobin + PO (observed) | 7.8 | 34.7* | 28* | 4.1 |
| orysastrobin + PO (expected) | 7.5 | 11.4 | 18.2 | 3.5 |
| synergy factor | 1.04 | 3.04 | 1.54 | 1.17 |
| p-value observed vs expected | 0.89 | 0.023 | 0.044 | 0.91 |
| kresoxim methyl | 6.7 | 4.1 | 7.3 | 3.2 |
| PO | 2.8 | 3.2 | 2.6 | 2.4 |
| kresoxim methyl + PO (observed) | 9.1 | 19.9* | 7.8 | 5.8 |
| kresoxim methyl + PO (expected) | 9.5 | 7.3 | 9.9 | 5.6 |
| synergy factor | 0.96 | 2.73 | 0.79 | 1.04 |
| p-value observed vs expected | 0.88 | 0.045* | 0.63 | 0.94 |
| dimoxystrobin | 12.4 | 18.9 | 7.6 | 4.1 |
| PO | 2.8 | 3.2 | 2.6 | 2.4 |
| dimoxystrobin + PO (observed) | 16.9 | 51.3* | 7.8 | 5.2 |
| dimoxystrobin + PO (expected) | 15.2 | 22.1 | 10.2 | 6.5 |
| synergy factor | 1.11 | 2.32 | 0.76 | 0.80 |
| p-value observed vs expected | 0.85 | 0.012* | 0.74 | 0.92 |
| fluoxastrobin | 8.6 | 5.6 | 3.3 | 1 |
| PO | 2.8 | 3.2 | 2.6 | 2.4 |
| fluoxastrobin + PO (observed) | 20.1* | 39.2* | 5.3 | 2.1 |
| fluoxastrobin + PO (expected) | 11.4 | 8.8 | 5.9 | 3.4 |
| synergy factor | 1.76 | 4.45 | 0.90 | 0.62 |
| p-value observed vs expected | 0.045* | 0.024* | 0.83 | 0.78 |
| picoxystrobin | 16.7 | 2.5 | 8.4 | 8.9 |
| PO | 2.2 | 3.2 | 2.6 | 2.4 |
| picoxystrobin + PO (observed) | 24.9 | 47.5* | 15.8* | 12.8 |
| picoxystrobin + PO (expected) | 18.9 | 5.7 | 11 | 11.3 |

-continued

|  | strobilurin w/v % | | | |
|---|---|---|---|---|
|  | $4 \times 10^{-7}$ | $1 \times 10^{-7}$ | $1 \times 10^{-8}$ | $1 \times 10^{-9}$ |
|  | PO w/v % | | | |
|  | $1 \times 10^{-7}$ | $1 \times 10^{-7}$ | $1 \times 10^{-7}$ | $1 \times 10^{-7}$ |
|  | strobilurin:PO ratio | | | |
|  | 4:1 | 1:1 | 1:10 | 1:50 |
| Treatment | % PGE$_2$ Inhibition | | | |
| synergy factor | 1.32 | 8.33 | 1.44 | 1.13 |
| p-value observed vs expected | 0.67 | 0.0004* | 0.048* | 0.91 |

*indicates statistical significance (p value < 0.05 between observed and expected).

The top table contains the ranges for azoxystrobin analogues with PO.

| | strobilurin:PO | | | |
|---|---|---|---|---|
| | 4:1 | 1:1 | 1:10 | 1:50 |
| strobilurin:PO | Molar ratios | | | |
| azoxystrobin | 2.959 | 0.740 | 0.074 | 0.015 |
| trifloxystrobin | 2.923 | 0.731 | 0.073 | 0.015 |
| orysastrobin | 3.050 | 0.762 | 0.076 | 0.015 |
| kresoxim methyl | 3.809 | 0.952 | 0.095 | 0.019 |
| dimoxystrobin | 3.657 | 0.914 | 0.091 | 0.018 |
| fluoxastrobin | 2.602 | 0.650 | 0.065 | 0.013 |
| picoxystrobin | 3.250 | 0.812 | 0.081 | 0.016 |

In the present invention, there may be a) a strobilurin; b) a 2-pyridinol-N-oxide material wherein the ratio of a:b is from about 10:1 to about 1:20; wherein there is a synergistic anti-inflammatory/cellular stress activity.

Detersive Surfactant

The present invention may be present in the form of a shampoo, conditioner, or leave on treatment. The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Further, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

A. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The shampoo composition, conditioner compositions, and/or leave-on treatments described herein may comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

The present invention may be directed to use of strobiliurins in a personal care composition for improving inflammation and cellular stress conditions in skin, scalp and hair. The present invention may be directed to use of strobiliurins in a personal care composition for an anti-inflammatory benefit. The present invention may be directed to use of strobiliurins as claimed in present claim set for anti-inflammatory benefit. The present invention may be directed to a method of using a composition comprising a) a strobiliurin; b) a 2-pyridinol-N-oxide material; wherein the ratio of a:b is from about 4:1 to about 1:10 to provide a synergistic anti-inflammatory/cellular stress activity. The present invention may be directed to a method of using a composition comprising: a)) a strobiliurin; b) a 2-pyridinol-N-oxide material; wherein the ratio of a:b is from about 4:1 to about 1:10 to provide a synergistic anti-inflammatory/cellular stress activity wherein there is at least about a 20% reduction in PGE2 release compared to a baseline.

EXAMPLES

Non-Limiting Examples

The shampoo compositions illustrated in the following examples are prepared by conventional formulation and mixing methods. All exemplified amounts are listed as weight percents on an active basis and exclude minor materials such as diluents, preservatives, color percentages are based on weight unless otherwise specified.

Shampoo Examples

| Note | Component/Example | 1 | 2 | 3 | 4 |
|---|---|---|---|---|---|
| | Water | 82.3 | 82.9 | 85.6 | 85.8 |
| 1 | Sodium laureth-1 sulfate | 11 | 14 | 0 | 6 |
| 2 | Cocamidopropyl betaine | 1 | 0 | 0 | 7 |
| 3 | CMEA | 1 | 2 | 0 | 0 |
| 4 | Sodium lauroyl sarcosinate | 0 | 0 | 5 | 0 |
| 5 | Decyl glucoside | 0 | 0 | 5 | 0 |
| 6 | Sodium laureth sulfosuccinate | 0 | 0 | 3 | 0 |
| 7 | Hydroxypropyl Methylcellulose | 0.3 | 0.1 | 0.2 | 0 |
| 8 | 1,10-Decanediol | 0 | 0 | 0.1 | 0 |
| 9 | Piroctone olamine | 0.8 | 0.5 | 1 | 1 |
| | Azoxystrobin | 0.8 | 0 | 0 | 0.2 |
| | Trifloxystrobin | 0 | 0.5 | 0 | 0 |
| | Picoxystrobin | 0 | 0 | 0.1 | 0 |
| 10 | Ethylene glycol distearate | 1.8 | 0 | 0 | 0 |
| 11 | Dimethiconol | 1 | 0 | 0 | 0 |

All above are on active basis; e.g. 11% SLE1S would require an addition of 44% of a 25% active SLE1S solution. The below table explains each Note from the above table

| | | |
|---|---|---|
| 1 | Supplied at 25% active by Stepan |
| 2 | Supplied at 30% active by Evonik |
| 3 | Supplied at 85% active by BASF |
| 4 | Supplied at 30% active by Croda |
| 5 | Supplied as 50% active by BASF |
| 6 | Supplied as 35% active by Solvay |
| 7 | Supplied by Dow |
| 8 | Supplied by Symrise |
| 9 | Supplied by Clariant |
| 10 | Supplied by Evonik |
| 11 | Supplied by Wacker |

The following examples further describe and demonstrate non-limiting examples within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Conditioner Compositions (Wt %)

| Components | Ex. 5 | Ex. 6 | Ex. 7 | Ex. 8 | Ex. 9 | Ex. 10 |
|---|---|---|---|---|---|---|
| Behenyl trimethylammonium Chloride/IPA*1 | 3.42 | 3.42 | | | 2.85 | 3.42 |
| Stearylamidopropyl dimethylamine | | | 2.40 | 2.40 | | |
| Polysorbate 20 | 0.03 | | | | | 0.03 |
| L-glutamic acid | | | 0.77 | 0.77 | | |
| Citric acid | 0.22 | 0.10 | 0.20 | 0.30 | 0.06 | 0.22 |
| Cetyl alcohol | 1.67 | 1.67 | 2.50 | 2.50 | 1.67 | 1.67 |
| Stearyl alcohol | 4.18 | 4.18 | 4.50 | 4.50 | 4.18 | 4.18 |
| Piroctone Olamine | 0.25 | 0.80 | 0.50 | 0.25 | 0.15 | 0.08 |
| Azoxystrobin | | 0.016 | 0.05 | 1.00 | 0.30 | 0.32 |
| Trifloxystrobin | 0.25 | | | | | |
| Benzyl alcohol | 0.4 | 0.4 | 0.4 | 0.4 | 0.4 | 0.4 |
| Phenoxy ethanol | 0.4 | 0.4 | 0.4 | 0.4 | 0.4 | 0.4 |
| Sodium benzoate | 0.25 | 0.25 | 0.25 | 0.25 | 0.25 | 0.25 |
| Polydimethylsiloxane | 3.00 | | | 0.85 | 1.40 | |
| Deionized Water | q.s. to 100% | | | | | |
| pH | 4.1 | 4.9 | 5.0 | 4.2 | 5.9 | 5.9 |

Leave-on Treatment Examples

| Note | Component/Example | 11 | 12 | 13 | 14 | 15 | 16 | 17 | 18 | 19 | 20 |
|---|---|---|---|---|---|---|---|---|---|---|---|
|  | Water | 61.95 | 55.7 | 40.25 | 64.53 | 40.85 | 92.35 | 95.26 | 95.1 | 92.6 | 91.7 |
| 1 | Ethanol | 30 | 40 | 50 | 30 | 50 | 0 | 0 | 0 | 0 | 0 |
| 2 | 2-Pyrrolidinone, 1-ethenyl-,homopolymer | 3.5 | 0 | 4 | 0 | 0 | 2 | 0 | 2 | 0 | 0 |
|  | Azoxystrobin |  | 0.5 | 2 | 0.02 | 0.6 | 0.4 | 0.04 | 0.1 | 0.25 | 0.3 |
|  | Trifloxystrobin | 0.45 |  |  |  |  |  |  |  |  |  |
| 3 | Hydroxypropyl Methylcellulose | 0 | 0 | 0 | 2 | 0 | 0 | 0 | 0 | 2 | 0 |
| 4 | Hydroxypropyl Starch Phosphate | 0 | 0 | 0 | 0 | 5 | 0 | 0 | 0 | 0 | 3 |
| 5 | Menthol | 0.25 | 0.3 | 0.3 | 0.25 | 0.4 | 0.25 | 0.3 | 0.3 | 0.25 | 0.4 |
| 6 | Piroctone Olamine | 0.45 | 0.5 | 0.45 | 0.2 | 0.15 | 0.1 | 0.4 | 0.1 | 0.1 | 0.8 |
| 7 | Niacinamide | 2.5 | 2.5 | 2.5 | 2.5 | 2.5 | 2.5 | 2.5 | 0 | 2.5 | 2.5 |
| 8 | Caffeine | 0.1 | 0.1 | 0.1 | 0.1 | 0.1 | 0.1 | 0.1 | 0.1 | 0 | 0.1 |
| 9 | Panthenol | 0.1 | 0.1 | 0.1 | 0.1 | 0.1 | 0.1 | 0.1 | 0.1 | 0.1 | 0 |
| 10 | PEG-40 Hydrogenated Castor Oil | 0 | 0 | 0 | 0 | 0 | 1 | 1 | 1 | 1 | 1 |
| 11 | Propylene Glycol | 0 | 0 | 0 | 0 | 0 | 0.9 | 0 | 0.9 | 0.9 | 0 |
|  | Fragrance | 0.5 | 0.3 | 0.3 | 0.3 | 0.3 | 0.3 | 0.3 | 0.3 | 0.3 | 0.2 |

1 SD-40B 200 Alcohol from Pride Solvents
2 Flexithix from Ashland
3 Benecel K200M from Ashland
4 Structure XL from AkzoNobel
5 Menthol from Kerry Ingredients and Flavors
6 Piroctone Olamine from Clariant
7 Niacinamide from Lonza
8 Caffeine from Merck
9 D-Panthenol from BASF
10 Cremophor RH-40 from BASF
11 Propylene Glycol from Sigma Aldrich Product Forms The personal care compositions of the present invention may be presented in typical personal care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, pre-wash product, co-wash product, and personal cleansing products, and treatment products; and any other form that may be applied to hair or skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) a strobilurin;
   b) a 2-pyridinol-N-oxide material
   wherein the ratio of a:b is from about 10:1 to about 1:20;
   wherein there is a synergistic anti-inflammatory/cellular stress activity.

2. The personal care composition according to claim 1 wherein the anti-inflammatory benefit is measured as PGE2 activity.

3. The personal care composition according to claim 1 wherein the ratio of a:b is from about 4:1 to about 1:10.

4. The personal care composition according to claim 1 wherein the personal care composition is selected from group consisting of a shampoo, conditioner, leave-on, tonic and mixtures thereof.

5. The personal care composition according to claim 1 wherein the 2-pyridinol-N-oxide material is from about 0.05% to about 5%, by weight of the composition.

6. The personal care composition according to claim 1 wherein the 2-pyridinol-N-oxide material is from about 0.3% to about 3%, by weight of the composition.

7. The personal care composition according to claim 1 wherein the 2-pyridinol-N-oxide material is selected from the group consisting of 1-Hydroxy-4-methyl-6-(2,4,4-trimethylpentyl)-2-pyridone monoethanolamine salt, 6-Cyclohexyl-1-hydroxy-4-methyl-2(1H)-pyridone ethanolammonium salt, 6-[[p-chlorophenoxy) phenoxy]methyl]-1 hydroxy-4-methyl-pyridone.

8. The personal care composition according to claim 7 wherein the 2-pyridinol-N-oxide material is piroctone olamine.

9. The personal care composition according to claim 1 wherein the personal care composition further comprises azoxystrobin.

10. A method of using a personal care composition comprising
 a) a strobiliurin;
 b) a 2-pyridinol-N-oxide material;
 wherein the ratio of a:b is from about 4:1 to about 1:10 to provide a synergistic anti-inflammatory/cellular stress activity.

11. A method of using a personal care composition comprising:
 a) a strobiliurin;
 b) a 2-pyridinol-N-oxide material;
 wherein the ratio of a:b is from about 4:1 to about 1:10 to provide a synergistic anti-inflammatory/cellular stress activity wherein there is at least about a 20% reduction in PGE2 release compared to a baseline.

* * * * *